(12) United States Patent
Nakamura

(10) Patent No.: US 6,530,686 B1
(45) Date of Patent: Mar. 11, 2003

(54) DIFFERENTIAL SCANNING CALORIMETER HAVING LOW DRIFT AND HIGH RESPONSE CHARACTERISTICS

(75) Inventor: Nobutaka Nakamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/319,624

(22) PCT Filed: Dec. 1, 1998

(86) PCT No.: PCT/JP98/05412
§ 371 (c)(1),
(2), (4) Date: Sep. 23, 1999

(87) PCT Pub. No.: WO99/28732
PCT Pub. Date: Jun. 10, 1999

(30) Foreign Application Priority Data

Dec. 1, 1997 (JP) ............................................. 9/330650

(51) Int. Cl.⁷ .......................... G01N 25/20; H05B 1/02; H05B 3/02
(52) U.S. Cl. .......................... 374/11; 374/34; 219/494; 219/497; 219/505
(58) Field of Search ............................... 374/10, 11, 12, 374/31, 33, 34; 219/497, 494, 505, 504

(56) References Cited

U.S. PATENT DOCUMENTS

| | | | | |
|---|---|---|---|---|
| 3,033,020 A | * | 5/1962 | Pakulak, Jr. et al. | 374/12 |
| 3,263,484 A | * | 8/1966 | Watson et al. | 374/11 |
| 4,783,174 A | * | 11/1988 | Gmelin et al. | 374/33 |
| 5,098,196 A | * | 3/1992 | O'Neill | 374/11 |
| 5,288,147 A | * | 2/1994 | Schaefer et al. | 374/31 |
| 5,672,289 A | * | 9/1997 | O'Neill | 374/11 |
| 5,842,788 A | * | 12/1998 | Danley et al. | 374/12 |
| 6,079,873 A | * | 6/2000 | Cavicchi et al. | 374/12 |

FOREIGN PATENT DOCUMENTS

| | | | | |
|---|---|---|---|---|
| DE | 19854649 A1 | * | 11/1998 | 374/11 |
| JP | 1-165944 | * | 6/1989 | G01N/25/00 |
| JP | 5-14202 | * | 4/1993 | G01N/25/20 |
| JP | 8-334482 | * | 12/1996 | G01N/25/00 |

* cited by examiner

Primary Examiner—Diego Gutierrez
Assistant Examiner—Stanley J. Pruchnic, Jr.
(74) Attorney, Agent, or Firm—Adams & Wilks

(57) ABSTRACT

The sample temperature is roughly controlled according to a program temperature by a furnace temperature controller, and at the same time precisely controlled by a detector temperature controller. Also, if a temperature difference occurs, the supply powers to heaters separately provided close to the sample and reference are adjusted such that the temperature difference is returned to zero by a differential heat compensating circuit, outputting a difference in supply power as a differential heat flow.

12 Claims, 2 Drawing Sheets

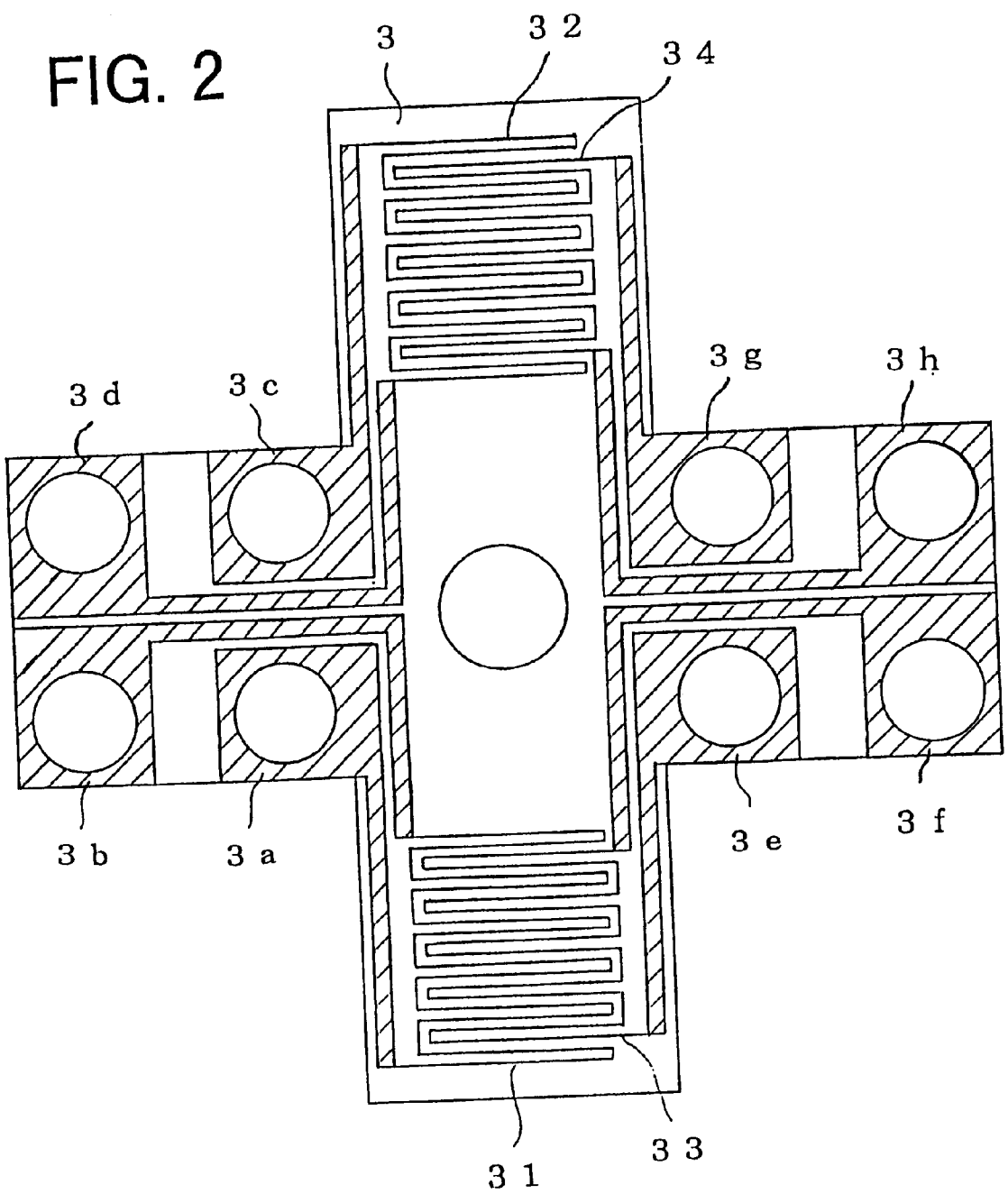

DIFFERENTIAL SCANNING CALORIMETER HAVING LOW DRIFT AND HIGH RESPONSE CHARACTERISTICS

TECHNICAL FIELD

The present invention relates to a thermal analysis apparatus used to measure how a physical or chemical property of a sample varies with temperature. More particularly, the invention relates to a differential scanning calorimeter to measure and analyze heat flow excessively generated or absorbed by a sample as compared with a reference when the temperature is varied at a constant rate.

BACKGROUND OF THE INVENTION

The differential scanning calorimeter is an apparatus which, when a sample and a reference substance (thermally stable substance, usually alumina or the like is used) are symmetrically placed and the temperatures of both are varied at a constant rate, detects and analyzes differentially a heat flow excessively generated or absorbed by the sample as compared with the reference substance.

When the temperature of a sample is raised at a constant rate, heat absorption by the sample increases with an increase in heat capacity of the sample. That is, a differential heat flow signal increases in absolute value. At this time, the absolute value of the differential heat flow signal is proportional to the heat capacity difference between the sample and the reference and the temperature increase rate. Consequently, the heat capacity of the sample can be determined from the differential heat flow signal based on the known temperature increase rate and reference heat capacity.

Meanwhile, when the sample fuses, the heat absorption by the sample temporarily increases. If making a graph on differential heat flow signals recorded in time series, the differential heat flow signals depict an endothermic peak. Also, if following a similar recording method, when crystallization is caused in the sample, the differential heat flow signals depict an exothermic peak. The area of such endothermic or exothermic peak, which is depicted against a time axis set to have a unit time corresponding to a constant length, is proportional to a heat amount released or absorbed (transition heat) upon transition of the sample. Accordingly, if the differential heat flow signal value is calibrated by measuring a known transition heat, it is easy to determine a transition heat of the sample from the differential heat flow signal.

In order to obtain a differential heat flow signal with useful properties as above, the differential scanning calorimeter is broadly used for analyzing a variety of materials. The conventional differential scanning calorimeter is roughly divided into the following two types One is called a power compensation type. It is structured by a combination of two symmetrically formed independent calorimeters for a sample and a reference, and both are provided with a resistance temperature sensor and heat flow feedback heater. The average value of temperatures detected by the both temperature sensors is compared with a temperature output of a temperature programmer which varies at a constant rate. Two calorimeters are heated up such that the both are brought into coincidence by the heat flow feedback heaters. Also, if a difference is caused in temperature output of the both temperature sensors, the both heaters are immediately increases or decreased in power to return the difference to zero. Thereupon, the difference of power supplied to the both heaters every second is recorded as a differential heat flow signal.

The other is called a heat flux type. It has a heat sink formed of a thermally good conductor within which sample and reference temperature sensors are fixed to form heat paths that are symmetric with and equivalent to each other. The heat sink temperature is compared with the temperature output of a temperature programmer varying at a constant rate, and feedback-controlled by a heater wound around the heat sink such that both are brought into coincidence. The temperature difference between the sample and the reference is detected by a differential thermocouple. On this occasion, if the temperature difference between the sample and the reference is divided by a thermal resistance between the heat sink and the sample, it is possible to determine a differential heat flow as a difference in heat flow to the sample and the reference in a similar procedure to a determination of current by dividing potential difference by resistance. That is, in the heat flux type differential scanning calorimeter, amplification is appropriately made on an output of the differential thermocouple representative of a temperature difference between the sample and the reference to output and record as differential heat flow signals.

The power compensation type differential scanning calorimeter is excellent in responsiveness and can realize a heat compensation time constant of less than two seconds. However, as for the baseline performance, there has been a difficulty in obtaining the same stability as in the heat flux type differential scanning calorimeter. The main reason of this lies in that the power compensation type sensor has a large temperature difference from surrounding members during measurement with a result that a comparatively large amount of heat leak occurs uninterruptedly from the sensor to the outside, causing a drift factor in the baseline. On the other hand, the heat flux type differential scanning calorimeter is excellent in baseline stability, but has a heat compensation time constant exceeding three seconds. Accordingly, there have been the disadvantages that the heat flow signal is blunted at its peak, a plurality of peaks are worsened in separation, and so on.

DISCLOSURE OF THE INVENTION

In order to solve the above problem, the present inventions comprises: a heat sink formed of a thermally good conductor shaving a space for accommodating a sample at an inside thereof: a detector fixed within the heat sink and formed by an insulating substrate formed with symmetric circuit patterns of metal resistors; a temperature measuring circuit for measuring a temperature of the detector by detecting resistance values of the metal resistors in the detector; a differential temperature detecting circuit for comparing resistance values of one pair of metal resistance circuits to detect a temperature difference between a sample and a reference placed in the detector; a program temperature function generator for outputting temperature target values in time; a heat sink temperature controller for controlling a temperature of the heat sink depending on an output of the program temperature function generator; a detector temperature controller for controlling a temperature of the detector by controlling a current value flowing through the metal resistance circuit in the detector based on a comparison result of an output of the program temperature generator and an output of the temperature measuring circuit; and a differential heat compensating circuit for causing a proper current to flow through each of the one pair of metal resistors in the detector such that an output of the differential temperature detecting circuit uninterruptedly returns to zero.

The sample and the reference are roughly controlled by heat conduction through a detector from the heat sink that is controlled in temperature depending on the program temperature. Also, the temperature of the reference is precisely controlled to be brought into coincidence with the program temperature by the detector temperature controller. Furthermore, if a temperature difference occurs between the sample and the reference, the supply power to the heaters separately provided close to the sample and reference is adjusted by the differential heat compensating circuit such that the temperature difference is immediately returned to zero.

As a result of this, both the sample and reference are controlled in temperature according to the program temperature.

The difference in heat generation or absorption of the sample in comparison with the reference is detected as a difference of supply power to the heaters separately provided close to the sample and reference, thus effecting a function as a differential scanning calorimeter.

BRIEF DESCRIPTION OF THE DRAWINGS

FIG. 2 is a pattern view of a detector used in the embodiment.

BEST MODE TO CARRY OUT THE INVENTION

Figure 1:
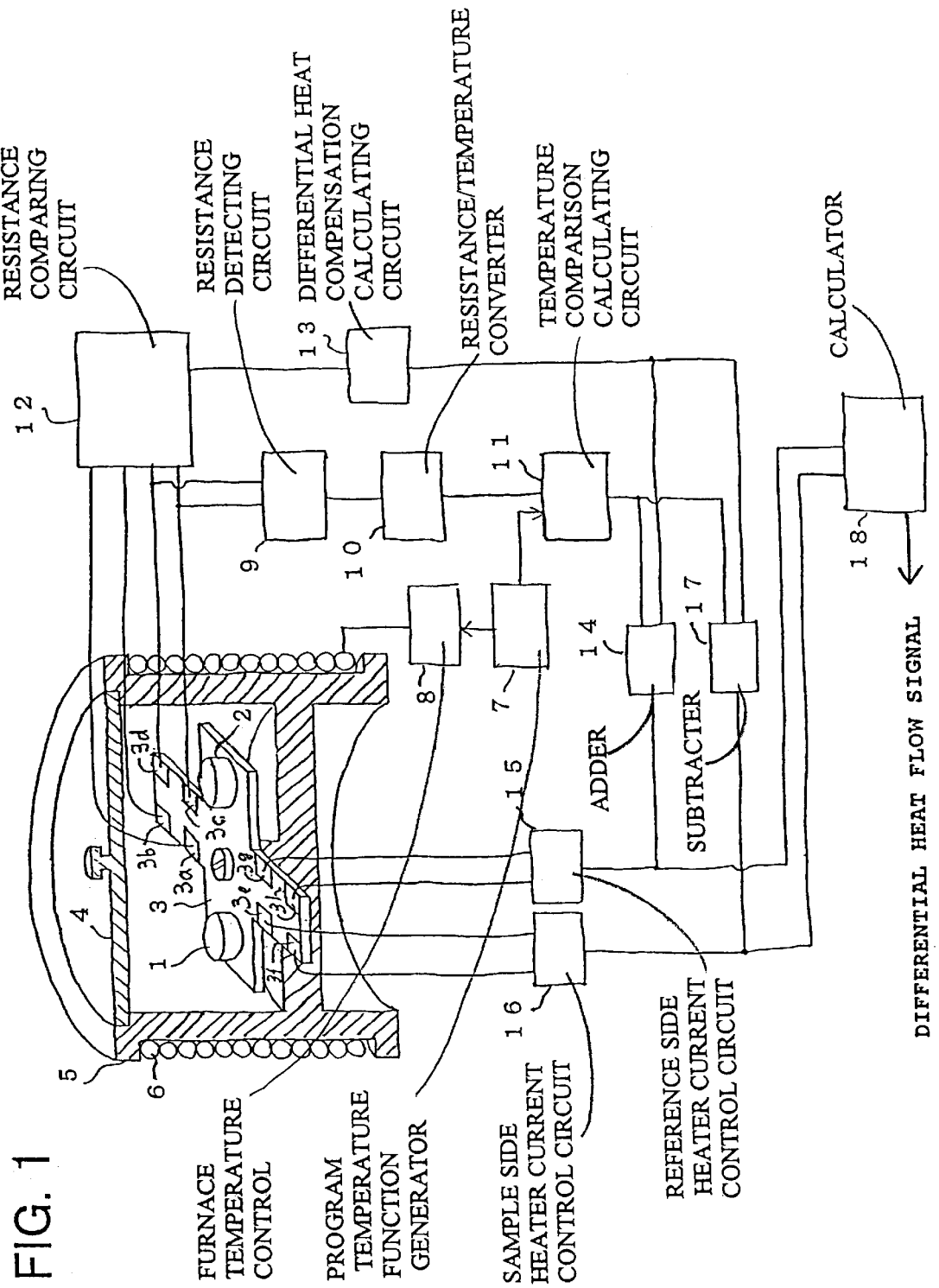
FIG. 1 is a block diagram partly having a sectional view showing one embodiment of the present invention.

Explanations will be made of an embodiment hereunder based on an embodiment shown in the drawings.

In FIG. 1, reference numeral 1 is a sample vessel containing a sample and 2 is a reference vessel containing a thermally stable reference substance. The sample vessel 1 and the reference vessel 2 are rested on a detector 3 formed by a alumina flat sheet in a cross shape with a platinum circuit pattern. The detector 3 is screwed with inconel-made screws to a central portion of a silver-made heat sink 5 that is cylindrical and almost sectionally in an H-character shape. The heat sink 5 has, at an upper portion, a silver-made heat sink lid 4. By the heat sink 5 and the heat sink lid 4, the sample vessel 1, the reference vessel 2 and the detector 3 are enclosed. The heat sink 5 has an insulation-coated furnace temperature control heater 6 wound on a lateral surface thereof.

A furnace temperature control circuit 8 is connected to a program temperature function generator 7 to generate program temperature signals for thermal analysis. The furnace temperature control circuit 8 properly adjusts an output of the furnace temperature control heater 6 connected to the furnace temperature control circuit 8 so that the temperature of the heat sink 5 varies corresponding to the program temperature function.

On the other hand, the detector 3 is provided with in total 8 terminals consisting of sample side measuring temperature resistance terminals 3a and 3b, reference side measuring temperature resistance terminals 3c and 3d, sample side compensating heater terminals 3e and 3f and reference side compensating heater terminals 3g and 3h.

Also, as shown in FIG. 2, the detail of the detector 3 is divided as a sample side and a reference side, besides terminals 3a–3h, to have a sample side measuring temperature resistance pattern 31 and a sample side compensating heater pattern 33 on the sample side, and a reference side measuring temperature resistance pattern 32 and a reference side compensating heater pattern 34 on the reference side.

Each pattern 31–34 is coated, at its surface, with a glaze (not shown) in a thin film form, keeping surface insulation.

Each terminal 3a–3h is provided with a small hole. Each terminal 3a–3h is mechanically fixed with a silver lead wire by a 1.6 mm screw and nut (not shown) made of silver.

Incidentally, the connection of each terminal 3a–3h with the lead wire may be substituted by a brazing treatment using a high temperature silver braze BAg-8 or the like, due to consideration of heat resistance.

As shown in FIG. 1, the reference side measuring temperature resistance terminals 3c, 3d are connected to a resistance detecting circuit 9, while the resistance detecting circuit 9 is connected to a resistance/temperature converter 10. The program temperature function generator 7 and the resistance/temperature converter 10 are connected to a temperature comparison calculating circuit 11.

The sample side measuring temperature resistance terminals 3a, 3b and the reference side measuring temperature resistance terminals 3c, 3d are both connected to the resistance comparing circuit 12, while the resistance comparing circuit 12 is connected to a differential heat compensation calculating circuit 13.

The temperature comparison calculating circuit 11 and the differential heat compensating circuit 13 are respectively connected to an adder 14 and a subtracter 17. The adder 14 is connected a reference side heater current control circuit 15, while the a subtracter 17 is connected to a sample side heater current control circuit 16. The outputs of the respective heater current control circuits 15, 16 are respectively sent to the reference side compensating heater terminals 3g and 3h and the sample side compensating heater terminals 3e and 3f, thereby controlling currents respectively flowing between both terminals. Therefore, the reference side heater current control circuit 15 and the sample side heater current control circuit 16 operates to increase a value of current flowing between the reference side compensating heater terminals 3g, 3h when the sample temperature becomes higher as compared with the reference, and at the same time decrease a value of current flowing between the sample side compensating heater terminals 3e, 3f.

A calculator 18 is connected to the sample side heater current control circuit 16 and the reference side heater current control circuit 15, and calculates a difference in consuming power per time between consumption by the sample side measuring temperature resistance pattern 31 and the reference side measuring temperature resistance pattern 32 based on the inputs to the respective circuits 15, 16, and outputs a differential heat flow signal.

Next, the operation of the apparatus shown in FIG. 1 will be explained.

First, a measurer opens the heat sink lid 4, and puts a sample vessel 1 packed with a sample to be measured and a reference vessel 2 packed with a reference substance having been confirmed of thermal stability in a temperature range to be measured at predetermined positions on the detector 3, closing the heat sink lid 4.

Next, following a measurement starting instruction of the measurer, program temperature signals input by the measurer are output from the program temperature function generator 7. One set of the program temperature signals output from the program temperature function generator 7 is sent to the furnace temperature control circuit 8, and is controlled such that the temperature of the heat sink 5 becomes 92% in absolute temperature due to the action of the furnace temperature control circuit 8. Consequently, the temperature of the heat sink 5 is controlled to always be somewhat lower than the program temperature. Incidentally, when measuring at a temperature below room temperature, a not-shown cooling member is appropriately used together. In such a case, however, the temperature of the heat sink 5 is still controlled to be lower than the program temperature.

Because the heat sink 5 is made of silver, which is a thermally good conductor, if a temperature gradient is caused within the heat sink 5, heat transfer immediately occurs to eliminate a temperature distribution. The heat from the heat sink 5 is conveyed to the detector 3 fixed at a central portion of the heat sink 5. The heat propagates through the detector 3 to the sample within the sample vessel 1 and the reference substance within the reference vessel 2. As a result, the sample and the reference substance are controlled approaching 92% of the program temperature in absolute temperature unit.

The temperature of the reference vessel 2 is detected by a resistance value of a reference side temperature detecting resistance pattern 32 (see FIG. 2) of the detector 3 placed at a lower portion. That is, the reference side measuring temperature resistance terminals 3c, 3d formed at an opposite end of the reference side measuring temperature resistance pattern 32 are connected to the resistance detecting circuit 9. The resistance value detected by the resistance detecting circuit 9 is converted into a temperature signal by the resistance/temperature converter 10, becoming a signal representative of a temperature of the reference vessel 2.

The temperature signal output by the program temperature function generator 7 and the temperature signal output by the resistance/temperature converter 10 are compared by the temperature comparison calculating circuit 11, and a predetermined calculation is preformed on the comparison result. Stating more concretely the operation of the temperature comparison calculating circuit 11, a well-known PID (proportion.integration.differential) device is subjected to a difference between the outputs of the temperature function generator 7 and the resistance/temperature converter 10, outputting a calculation result.

The output of the temperature comparison calculating circuit 11 is sent through the adder 14 and the subtracter 17 respectively to the reference side heater current control circuit 15 and the sample side heater current control circuit 16. The reference side heater current control circuit 15 causes a current to flow through the reference side compensating heater terminals 3g, 3h to the reference side compensating heater pattern 34 (see FIG. 2). The sample side heater current control circuit 16 causes a current equal to the reference side through the sample side compensating heater terminals 3e, 3f to the sample side compensating heater pattern 33 (see FIG. 2). A series connection consisting of a configuration formed by the reference side measuring temperature resistance pattern 32, resistance detecting circuit 9, resistance/temperature converter 10, program temperature function generator 7, temperature comparison calculating circuit 11, reference side heater current control circuit 15 and reference side compensating heater pattern 34 forms a negative feedback loop, and operates to bring the temperature of the reference vessel 2 into agreement with the program temperature. That is, the first negative feedback loop operates to eliminate a deviation of about 8% in absolute temperature unit as a difference between the program temperature and the reference temperature.

On the other hand, temperatures of the sample vessel 1 and the reference vessel 2 are respectively detected by resistance values of the sample side measuring temperature resistance pattern 31 (see FIG. 2) and the reference side measuring temperature resistance pattern 32, and compared by the resistance comparing circuit 12. The resistance comparing circuit 12 is configured by a bridge circuit (not shown). The output signal of the resistance comparing circuit 12 represents a difference in resistance value between the sample side measuring temperature resistance pattern 31 and the reference side measuring temperature resistance pattern 32. Also, the resistance difference signal as an output of the resistance comparing circuit 12 is representative of a temperature difference between the sample vessel 1 and the reference vessel 2. Accordingly, the output of the resistance comparing circuit 12 may be dealt with as a well-known differential thermal analysis (DTA) signal.

The output of the resistance comparing circuit 12 is sent to the differential heat compensation calculating circuit 13 where it is subjected to proportional calculation (amplification) and is thereafter output to the adder 14 and the subtracter 17. The adder 14 and the subtracter 17 respectively output a sum and a difference of outputs of the temperature comparison calculating circuit 11 and the differential heat compensation calculating circuit 13 individually to the reference side heater current control circuit 15 and the sample side heater current control circuit 16, controlling the currents to the sample side compensating heater pattern 33 and the reference side compensating heater pattern 34. A series connection consisting of a configuration formed by the sample side measuring temperature resistance pattern 31, reference side measuring temperature resistance pattern 32, resistance comparing circuit 12, differential heat compensation calculating circuit 13, reference side heater current control circuit 15, sample side heater current control circuit 16, sample side compensating heater pattern 33 and reference side compensating heater pattern 34, as a whole, forms a second feedback loop, and continues operation to bring close the temperatures of the sample vessel 1 and the reference vessel 2, with a result that the temperatures of the both are always almost in agreement.

In the course of a measurement to raise the temperature at a constant rate, if a transition with heat release or absorption occurs in the sample, the temperature of the sample behaves to temporarily rise or fall to cause a temperature difference between the sample vessel 1 and the reference vessel 2. This difference is immediately returned to zero by the second negative feedback loop. Consequently, it can be known what degree the sample excessively absorbed or dissipated heat as compared with the reference substance by determining a difference in electric power (resistance value×square of current value) consumed by the sample side compensating heater pattern 33 and the reference side compensating heater pattern 34.

This electric power difference is calculated by the calculator 18, and outputted as a differential heat flow signal to be used for analysis on the sample, thus realizing a function as a differential scanning calorimeter.

INDUSTRIAL APPLICABILITY

As the above, according to the present invention, the temperatures of a sample and a reference is roughly controlled by a furnace temperature controller and at the same time accurately controlled to be coincident with a program temperature by a detector temperature controller. Also, if a temperature difference between the sample and the reference occurs, the supply powers to the heaters separately provided close to the sample and the reference are adjusted to immediately return the temperature difference to zero by a differential heat compensating circuit. The difference in supply power is outputted as a differential heat flow.

As a result of this, because the temperature difference between the sample or reference and the heat sink surrounding them is small, the sample or reference is thermally insulated from the outside and their direct heat exchange to and from the outside is suppressed. Thus, an effect is obtained that drift hardly occurs in the differential heat flow signal and the defect of the power compensation type differential scanning calorimeter is eliminated.

Also, where a transition with heat release or absorption occurs in the sample, the power supplies to the heaters separately provided close to the sample and the reference can be controlled such that the temperature difference is immediately returned to zero by the differential heat compensating circuit. Moreover, the proportional coefficient as a control parameter at that time can be optimally controlled. Thus, an effect is obtained that a highly responsive differential heat flow signal is available and the defect of the heat flux type differential scanning calorimeter is also eliminated.

What is claimed is:

1. A differential scanning calorimeter, comprising: a heat sink formed of a thermally conductive material and having an internal space for accommodating a sample; a detector fixed within the heat sink and formed by an insulating substrate having formed thereon a plurality of symmetric circuit patterns of metal resistors; a temperature measuring circuit for measuring a temperature of the detector by detecting a resistance value of at least one of the metal resistors in the detector; a differential temperature detecting circuit for comparing resistance values of one pair of symmetric metal resistors to detect a temperature difference between a sample and a reference placed on the detector, each in proximity to a respective one of the one pair of symmetric metal resistors; a program temperature function generator for outputting temperature target values in a time sequential manner; a heat sink temperature controller for controlling a temperature of the heat sink depending on an output of the program temperature function generator; a detector temperature controller for controlling a temperature of the detector by controlling currents flowing through the metal resistors in the detector based on a comparison result of an output of the program temperature generator and an output of the temperature measuring circuit; a differential heat compensating circuit for causing a proper current to flow through one pair of symmetric metal resistors in the detector such that an output of the differential temperature detecting circuit is reduced toward zero; whereby a low drift characteristic and a high responsiveness are both obtained.

2. A differential scanning calorimeter according to claim 1; wherein the temperature of the detector is negatively feedback-controlled to be brought into coincidence with a target temperature output by the program temperature function generator, and the temperature of the heat sink is negatively feedback-controlled to between 80% and 100% in absolute temperature with respect to the target temperature output from the program temperature function generator.

3. A differential scanning calorimeter according to claim 2; wherein the metal resistors, the temperature measuring circuit, the program temperature function generator and the detector temperature controller are connected to form a first feedback loop for negatively feedback-controlling the temperature of the detector to be maintained at the target temperature value output by the program temperature function generator.

4. A differential scanning calorimeter according to claim 2; wherein the metal resistors, the differential temperature detecting circuit and the differential heat compensating circuit are connected to form a second feedback loop for controlling the detector temperature to eliminate a differential temperature between the one pair of metal resistors.

5. A differential scanning calorimeter according to claim 1; wherein the detector has a first pair of symmetrically arranged metal resistors on which the sample and the reference are disposed when in use, the temperature measuring circuit is connected to the metal resistor on which the reference is disposed to measure the temperature of the detector in the vicinity of the reference, and the differential temperature detecting circuit is connected to each of the first pair of metal resistors to detect a differential temperature between the reference and the sample.

6. A differential scanning calorimeter according to claim 5; wherein the detector further comprises a second pair of symmetrically arranged metal resistors each being disposed proximate a respective one of the first pair of metal resistors, the second pair of metal resistors being connected to the differential heat compensating circuit to control currents flowing in the second pair of metal resistors to eliminate a differential temperature between the reference and the sample.

7. A differential scanning calorimeter according to claim 1; wherein the heat sink is formed of a material having a thermal conductivity sufficient to eliminate a temperature gradient thereacross.

8. A differential scanning calorimeter according to claim 7; wherein the heat sink is formed of silver.

9. A differential scanning calorimeter according to claim 1; wherein the detector is connected to the heat sink so that heat is transferred from the heat sink through the metal resistors formed on the detector to uniformly heat the sample and the reference disposed on the detector.

10. A differential scanning calorimeter, comprising: a heat sink formed of a thermally conductive material and defining an internal chamber for accommodating a sample and a reference substance; a detector fixed within the internal chamber and comprising an insulating substrate and a pair of symmetrically arranged resistor patterns formed thereon, one resistor pattern being formed in close proximity to each of the sample and the reference substance; a first heater for heating the heat sink to a desired temperature to heat the sample and the reference substance; a second heater for heating the resistor patterns to control a temperature of the detector; a first control circuit for detecting the detector temperature, comparing the detector temperature with the desired temperature, and controlling the second heater to control a current flowing through the resistor patterns to eliminate a difference between the desired temperature and the detector temperature; and a second control circuit for monitoring the temperature of the resistor patterns, comparing the temperatures of the resistor patterns, and controlling the currents flowing through the resistor patterns to eliminate a temperature difference therebetween.

11. A differential scanning calorimeter according to claim 10; wherein the first control circuit comprises a program temperature function generator for outputting desired temperature values in a time sequential manner, a temperature measuring circuit for measuring a temperature of the detector by detecting a resistance value of the resistor patterns, a heat sink temperature controller for controlling a temperature of the heat sink depending on an output of the program temperature function generator, and a detector temperature controller for controlling a temperature of the detector by controlling current flowing through the resistor patterns based on a comparison result of an output of the program temperature generator and an output of the temperature measuring circuit.

12. A differential scanning calorimeter according to claim 11; wherein the second control circuit comprises a differential temperature detecting circuit for comparing resistance values of the pair of resistor patterns to detect a temperature difference between the sample and the reference substance placed in the detector, and a differential heat compensating circuit for controlling currents flowing through the resistor patterns such that an output of the differential temperature detecting circuit is reduced.

* * * * *